United States Patent
Larsen

[11] Patent Number: 5,910,445
[45] Date of Patent: Jun. 8, 1999

[54] SYSTEM FOR THE DETECTION OF PROTEIN CONTAMINATION ON AN ELECTRODE

[75] Inventor: Eiler Larsen, Brondby, Denmark

[73] Assignee: Rolic AG, Zug, Switzerland

[21] Appl. No.: 07/741,984

[22] Filed: Aug. 6, 1991

Related U.S. Application Data

[63] Continuation of application No. 07/221,792, filed as application No. PCT/DK87/00149, Dec. 2, 1987, abandoned.

[30] Foreign Application Priority Data

Dec. 3, 1986 [DK] Denmark ................................. 5806/86

[51] Int. Cl.[6] ...................................................... G01N 33/48
[52] U.S. Cl. ............................................. 436/5; 436/8
[58] Field of Search ................... 73/1 R; 436/8–19, 436/5–6

[56] References Cited

U.S. PATENT DOCUMENTS

| | | | |
|---|---|---|---|
| 4,358,424 | 11/1982 | Weber et al. | 422/50 |
| 4,363,633 | 12/1982 | Christiansen | 436/18 |
| 4,410,631 | 10/1983 | Czaban et al. | 436/8 |
| 4,626,512 | 12/1986 | Oku et al. | 436/18 |
| 4,753,888 | 6/1988 | Chiang | 436/19 |
| 4,806,486 | 2/1989 | Sprokholt et al. | 436/18 |

FOREIGN PATENT DOCUMENTS 0190791  8/1986  European Pat. Off. .

OTHER PUBLICATIONS

Henry et al. : Clinical Chemistry, Principles and Technics 2nd Ed. Harper & Row, Hagerstown, MD, 1974 p. 774.
Fisher '86, IL System 1301 PH/Blood Gas Analyzer p. 310.
Merzon et. al., Study of Blood Serum Electrolyte Levels Using Ion–Selective Electrode, Ionnyi. Obmen Ionometriya. 2, 191–202, 1979 (See Abstract, Chem. Abs., 92 (236 193743a.

*Primary Examiner*—Lyle A. Alexander
*Attorney, Agent, or Firm*—Bryan Cave LLP

[57] ABSTRACT

The use of an aqueous, synthetic composition containing $Ca^{++}$ and having a controlled, specified pH value for revealing the presence of protein contamination on the membrane of a pH measuring electrode.

3 Claims, 4 Drawing Sheets

SYSTEM FOR THE DETECTION OF PROTEIN CONTAMINATION ON AN ELECTRODE

This is a continuation of U.S. application Ser. No. 07/221,792, filed Sep. 26, 1988, now abandoned.

The present invention relates to a new use of an aqueous synthetic composition having a controlled, specified pH value and comprising $Ca^{++}$ ions.

Compositions with a specified pH value and comprising a cationic component and in many instances with a specified oxygen partial pressure and a specified carbon dioxide partial pressure are widely used in the calibration and the quality control procedure of electrochemical measuring apparatuses, in particular those apparatuses intended for use in the medical field for measurement on physiological liquids such as whole blood, plasma, serum, urine.

The aim of using quality control compositions is to control the reliability of the measurements obtained by a measuring apparatus and in case of any malfunction to reveal, if possible, which type of malfunction actually takes place.

Among the commercially available compositions for quality control of electrochemical measuring apparatuses are the aqueous phosphate based buffer solutions manufactured by Radiometer A/S, Copenhagen, Danmark, and sold under the trademarks S2350 QUALICHECK®; S2360 QUALICHECK®; QUALICHECK® Blood Gas—Acidemea, S2030; QUALICHECK® Blood Gas—Normal, S2040; QUALICHECK® Blood Gas—Alkalemia, S2050; and QUALICHECK® Blood Gas—High Oxygen, S2060.

The S2350 and S2360 solutions have specified values for pH and $Ca^{++}$ (concentration of $Ca^{++}$ ions) and each solution comprises a TES pH buffer system (TES is an abbreviation of N-tris (hydroxymethyl) methyl-2-aminoethane sulphonic acid), calcium chloride and sodium chloride.

The S2060 solution has specified values for pH, $K^+$ (concentration of potassium ions), $Po_2$ ( partial pressure of oxygen) and $Pco_2$ (partial pressure of carbon dioxide); the S2060 solution comprises a TES pH buffer system, sodium bicarbonate, potassium chloride and sodium chloride and is equilibrated with an oxygen and carbon dioxide containing gas. The S2030; S2040 and S2050 solutions, respectively, have specified values for the same parameters except $K^+$ and comprise a phosphate pH buffer system; otherwise these solution correspond to the S2060 solutions.

A very recent review article (Elser R. C., Respiratory Care, Sep. 1986, 31(9), 807) gives an excellent introduction to the problems encountered in the quality control of blood gas analysis and the article is incorporated herein by reference.

The quality control and calibration compositions—commonly designated reference liquids—have also been the subject of a number of articles and patents.

The following patents which disclose reference liquids for blood pH measurement are likewise incorporated herein by reference:

U.S. Pat. Nos. 3,380,929; 3,681,255; 3,859,049; 3,973,913; 4,001,142; 4,126,575; 4,151,108; 4,163,734; 4,199,471; 4,266,941; 4,279,775; 4,289,648; 4,299,728; 4,363,633; 4,369,127; 4,375,743; 4,397,392; 4,458,021; 4,469,792; 4,470,520; 4,485,174; British Patent Application No. GB 2031148 and German Offenlegungsschrift No. DE 3321100.

Two principally different groups of reference liquids exist, viz. one group of reference liquids based on blood or blood derived components and another group of purely synthetic reference liquids. The former group behaves to a great extent like blood. However, the handling is problematical due to their instability.

The purely synthetic reference liquids are generally more stable than the blood based reference liquids, but these compositions are unable to reveal certain types of apparatus malfunction which will lead to erroneous measurements when the apparatus is used for performing measurements on blood samples.

For example, it is well-known that most synthetic quality control solutions do not reveal the presence of protein contamination on the pH-sensitive membrane of a pH electrode. As the occurrence of protein contaminants on the pH electrode is a very common phenomenon it is inconvenient to use a reference fluid that does not reveal this source of error. The problems resulting from measurement of the pH-value of a blood sample with a pH glass electrode with a protein contamination on the active measuring surface of the glass electrode have been discussed i.a. by Matthews, H. R. et.al. at a lecture given at 10th International Congress of Clinical Chemistry, Mexico City, Mexico, Feb. 26–Mar. 3, 1978 and is a widely recognized problem in the art. In automated analyzers where the electrode potential after a predetermined period is used to establish sample pH regardless of whether the electrode response has stabilized by the end of that period, a lower measured pH value than the pH value measured with an uncontaminated electrode will be found.

On the contrary, when measuring the pH value of for example one of the above mentioned phosphate based control solutions the measured pH value will be essentially independent of the presence of protein contamination on the active measuring surface of the glass electrode. This means that the presence of protein contamination on the active measuring surface of the glass electrode will not be revealed by the phosphate based control solution despite the fact that the contamination will result in erroneous measuring results for a blood sample.

An object of the present invention is to provide a way of revealing the presence of protein contamination on a pH measuring electrode membrane in the quality control procedure of a blood pH measuring apparatus.

A further object of the invention is to provide an improved synthetic quality control system with ability to reveal the presence of such protein contamination.

Another object of the invention is to provide an improved automated blood pH measuring apparatus.

Applicant has now discovered that an aqueous synthetic composition having a controlled specified pH value and comprising an effective amount of $Ca^{++}$ ions can be used for revealing the presence of protein contaminants on the membrane of a pH measuring electrode.

This discovery is based on systematic experimental work involving addition of various blood components such as proteins, $Mg^{++}$ and $Ca^{++}$ to aqueous buffer solutions of known pH.

Applicant's work showed that the electrode response curves for a $Ca^{++}$ containing reference liquid and a blood sample, respectively, will be substantially identical regardless of whether the pH measuring electrode is contaminated with proteins or not. This finding has led to the conclusion that addition of $Ca^{++}$ ions in a suitable effective amount to a reference liquid will make the reference liquid more similar to blood and thus useable for checking the presence of protein contaminants on a pH measuring electrode.

Applicant's work also showed that addition of protein (albumin) and addition of $Mg^{++}$ ions did not provide the effect found by adding $Ca^{++}$ ions. Applicant contemplates that addition of other cations, e.g. $Cu^+$, $Fe^{++}$ $Co^{++}$ may provide the same effect as $Ca^{++}$ ions as these ions may be exchanged with $H^+$ ions in a similar manner as $Ca^{++}$ ions when exposed to the electrode contamination.

It should be mentioned that reference liquids having a specified pH value and comprising $Ca^{++}$ ions are disclosed in U.S. Pat. No. 4,363,633 and in U.S. Pat. No. 4,469,792.

The reference liquid according to U.S. Pat. No. 4,363,633 is described as useable for checking a pH electrode response and a $Ca^{++}$ electrode response at the same time; no effect of the $Ca^{++}$ ions on the pH measurement has been acknowledged in the patent specification or during the practical use of the corresponding commercial products (the above-mentioned S2350 QUALICHECK® and S2360 QUALICHECK® solutions).

U.S. Pat. No. 4,469,792 discloses a reference liquid comprising substantially pure stroma-free hemoglobin solution, a pH buffer system, a source of bicarbonate ions and predetermined amounts of gases found in blood. The idea of incorporating in the reference liquid according to U.S. Pat. No. 4,469,792 an electrolyte source of physiological nature, i.e. present in normal blood, such as sodium chloride, potassium chloride, calcium chloride is briefly mentioned in the specification of the said patent. However, neither the purpose of incorporating the electrolyte source in the liquid nor the actual amount of the electrolyte source is mentioned.

The amount of $Ca^{++}$ ions which should be incorporated in a quality control liquid to enable the solution to reveal the presence of protein contamination will depend, to some extent at least, on the composition of the quality control liquid; for example the buffer capacity of the control liquid may influence the level which should be chosen. The preferred levels of $Ca^{++}$ ions according to the invention will appear below.

The invention further comprises a method for revealing the presence of protein contamination on the membrane of a blood pH measuring electrode, said method comprising the steps of:

contacting the pH measuring electrode with a quality control liquid having a controlled, specified pH value and comprising an effective amount of $Ca^{++}$ ions;

comparing the pH value measured for the quality control liquid with the specified value;

using the outcome of the comparison to indicate whether or not protein contamination is present; taking a significantly lower measured pH value than the specified value as an indication of the presence of protein contamination on the blood pH measuring electrode membrane.

In a further aspect the invention relates to a blood pH measuring apparatus adapted for cooperation with a quality control liquid having a controlled specified pH value and comprising an effective amount of $Ca^{++}$ ions, said apparatus comprising: a pH electrode for measuring the pH value of liquid under test:

a chamber for accomodating liquid under test and being so positioned relative to the pH electrode that the liquid under test when accomodated in the chamber is exposed to the membrane of the pH electrode;

memory and data processing means;

means for identifying a measurement as a quality control measurement and means for input of the relevant specified pH value in the data processing means;

means for comparing the pH value actually measured with the corresponding specified value; and means for indicating the presence of a protein contamination on the pH electrode; the activation of said indicating means being controlled, at least partly, by the outcome of the said comparison between the measured pH value and the specified pH value.

Automated blood pH measurement apparatuses have long been known in the art. Such analyzers have been disclosed i.a. in U.S. Pat. No. 3,874,850; U.S. Pat. No. 4,160,714 and U.S. Pat. No. 4,415,534, the contents of which are incorporated herein by reference; and the assignee of the present invention has for more than 10 years marketed various models of such analyzers under the designation ABL Acid Base Laboratory. The members of the ABL-family measure pH, $Po_2$, $Pco_2$ and in some instances hemoglobin and potassium in whole blood. Furthermore, the ICA1 device marketed by the assignee of the present invention measures $Ca^{++}$ and pH in whole blood.

These analyzers are adapted for cooperation with quality control liquids and vice versa. Each batch of quality control liquid is provided with labelling specifying for each analyzer model a pH value, $pH_{ass}$, and corresponding control limits, $\Delta pH_{ass}$. The specified or assigned pH value and the control limits have been established on a statistical basis. In order to establish the assigned pH value and the control limits 200 samples in total from one and the same batch are measured. 10 analyzers are used, 5 samples per day per analyzer are measured and the measurements are repeated 4 times in total (on 4 different days).

A measurement value outside the interval $pH_{ass} \pm \Delta pH_{ass}$ is considered as clearly or significantly different from the specified value and is taken as an indication of some kind of analyzer malfunction. However, as previously mentioned, protein contamination on the pH electrode will not be revealed when using known synthetic quality control liquids as the pH value of these synthetic quality control liquids is unaffected by protein contamination. Thus, the new use of $Ca^{++}$ containing quality control liquids disclosed herein has made it possible to provide blood pH analyzers with a new and highly desirable feature namely a message function informing the user that the pH electrode of the analyzer is contaminated.

In the blood pH measuring apparatus according to the present invention the means for identifying a measurement as a quality control measurement and the means for input of the relevant specified pH value in the data processing means may comprise one and the same means. It is further contemplated that these means may be activated without human interaction.

The finding that the measured pH value differs clearly or significantly from the specified pH value may form the sole criterion for activating the means for indicating the presence of protein contamination.

A safer decision concerning whether or not to activate the means indicating the presence of protein contamination on the pH measuring electrode membrane is obtained by adapting the analyzer to use as a further criterion the result of a comparison between the pH value measured on a further quality control liquid containing no $Ca^{++}$ ions or an amount of $Ca^{++}$ ions less than the minimum amount effective to shift the pH response of a protein contaminated pH electrode exposed to the liquid to a pH value significantly different from the specified value. Obtaining a measured pH value clearly different from the specified value for the first quality control liquid and a measured pH value corresponding to the specified value for the further quality control liquid indicates with a very high probability the presence of protein contamination on the pH electrode membrane as the source of error. Obtaining a clear difference between the measured pH value and the specified pH value for both quality control liquids indicates that the analyzer suffers from another error producing malfunction than protein contamination, for example dilution of the liquid under test with the rinse liquid normally drawn through the conduits of an automated analyzer between the tests.

In a still further aspect the present invention relates to a liquid quality control system comprising: a first quality control liquid having a controlled pH value and being provided with an assigned value, pH, and a corresponding assigned pH range, $pH \pm \Delta pH_1$ the controlled pH value being a value within the range of pH 6.6–8.0, said first quality control liquid further comprising $Ca^{++}$ ions in an amount greater than the minimum amount effective to shift the pH response obtained with a protein contaminated pH electrode from a value falling within the assigned pH range to a value falling outside the said assigned pH range;

a second quality control liquid having a controlled pH value and being provided with an assigned pH value, $pH_2$, and a corresponding assigned pH range, $pH_2 \pm \Delta pH_2$, the controlled pH value being a value within the range of pH 6.6–8.0; said second quality control liquid having a content of $Ca^{++}$ ions lower than the minimum amount effective to shift the pH response obtained with a protein contaminated pH electrode from a value falling within the assigned pH range, $pH_2 \pm \Delta pH_2$, to a value falling outside the said assigned pH range.

As described previously in connection with the improved analyzer according to the invention the use of a system comprising two quality control liquids, one with a level of $Ca^{++}$ ions higher than the minimum effective amount and the other with a level of $Ca^{++}$ lower than the minimum effective amount, will enable the user or the analyzer to conclude with very high certainty whether or not protein contamination is present on the pH electrode membrane.

In the liquid control system according to the invention the content of $Ca^{++}$ ions in the first quality control liquid is preferably greater than 0.1, such as 0.1–5.0 mmol/l; more preferably 0.2–3.0 mmol/l and most preferably 0.5–2.0 mmol/l.

In the liquid quality control system according to the invention the content of $Ca^{++}$ ion in the second quality control liquid is preferably less than 0.5 mmol/l; more preferably less than 0.3 mmol/l; still more preferably less than 0.1 mmol/l and most preferably the second quality control liquid is essentially without added $Ca^{++}$ ions.

Usually, the controlled pH value is obtained by a suitable pH buffer such as one of the various buffers decribed by Good N. E. et.al., Biochemistry 5 (1966) 467 or similar buffers containing sulphonic acid residues; or Triethanol Amine; Tris or Tricine buffer systems.

The control limits normally given for pH quality control liquids are usually within the range of 10 mpH–50 mpH, such as ±15 mpH.

The quality control liquids of the quality control system according to the invention will often be used in the control of analyzers measuring apart from pH other components or parameters such as $Po_2$; $Pco_2$; the content of various blood cations or anions ($K^+$, $Na^+$, $Li^+$, $Ca^{++}$, $Cl^-$, $HCO_3^-$); total hemoglobin or the various hemoglobins; metabolites such as glucose, urea, creatinine, lactate. Accordingly, incorporation of a controlled level of one or several of those components or parameters will often be preferred.

Thus, a preferred embodiment of the quality control system according to the invention comprises control liquids each having a controlled $Po_2$ value selected from the range of 20–400 mmHg; and a controlled $Pco_2$ value selected from the range of 10–140 mmHg and will be suitable for the quality control of pH/blood gas analyzers, such as the above-mentioned ABL's.

The $Po_2$ value is preferably stabilized by incorporating a so-called oxygen buffer such as a perfluoro compound in the quality control liqiuds. Details on such oxygen buffers are given i.a. in U.S. Pat. No. 4,163,734.

The $Pco_2$ value is preferably stabilized by incorporating together with the pH buffer bicarbonate ions in the quality control liquids.

The invention will now be further described in the example given below and in the drawing, wherein:

BRIEF DESCRIPTION OF THE DRAWINGS

FIG.1 shows the responses of an uncontaminated pH electrode and of a protein contaminated pH electrode, respectively, on exposure to a sample of whole blood. The upper curve of FIG. 1 shows the response obtained with the uncontaminated pH electrode (freshly cleaned by standing one hour in a cleaning solution comprising the alkaline detergent DECONEX® and deionized water in the ratio 1:4 w/w. The cleaning solution is provided by Radiometer A/S under the trade name S5332) and the lower curve shows the response obtained with a contaminated pH electrode. The measurements were carried out on an automated blood gas analyzer manufactured by Radiometer A/S, Copenhagen, and sold under the name ABL3—Acid Base Laboratory. The analyzer was operated according to the usual procedure and was connected to a recorder so as to obtain records of the electrode response variation with time. The arrows at the left side of the drawing indicate the time at which the electrode chain was formed by establishing contact between the salt bridge liquid of the apparatus and the sample. At a predetermined period of time (about 48 secs.) after the formation of the liquid junction (as indicated by the arrows at the right side of the drawing) the electrode response is automatically registered by the apparatus and used for the calculation of the sample pH.

Figure 1:
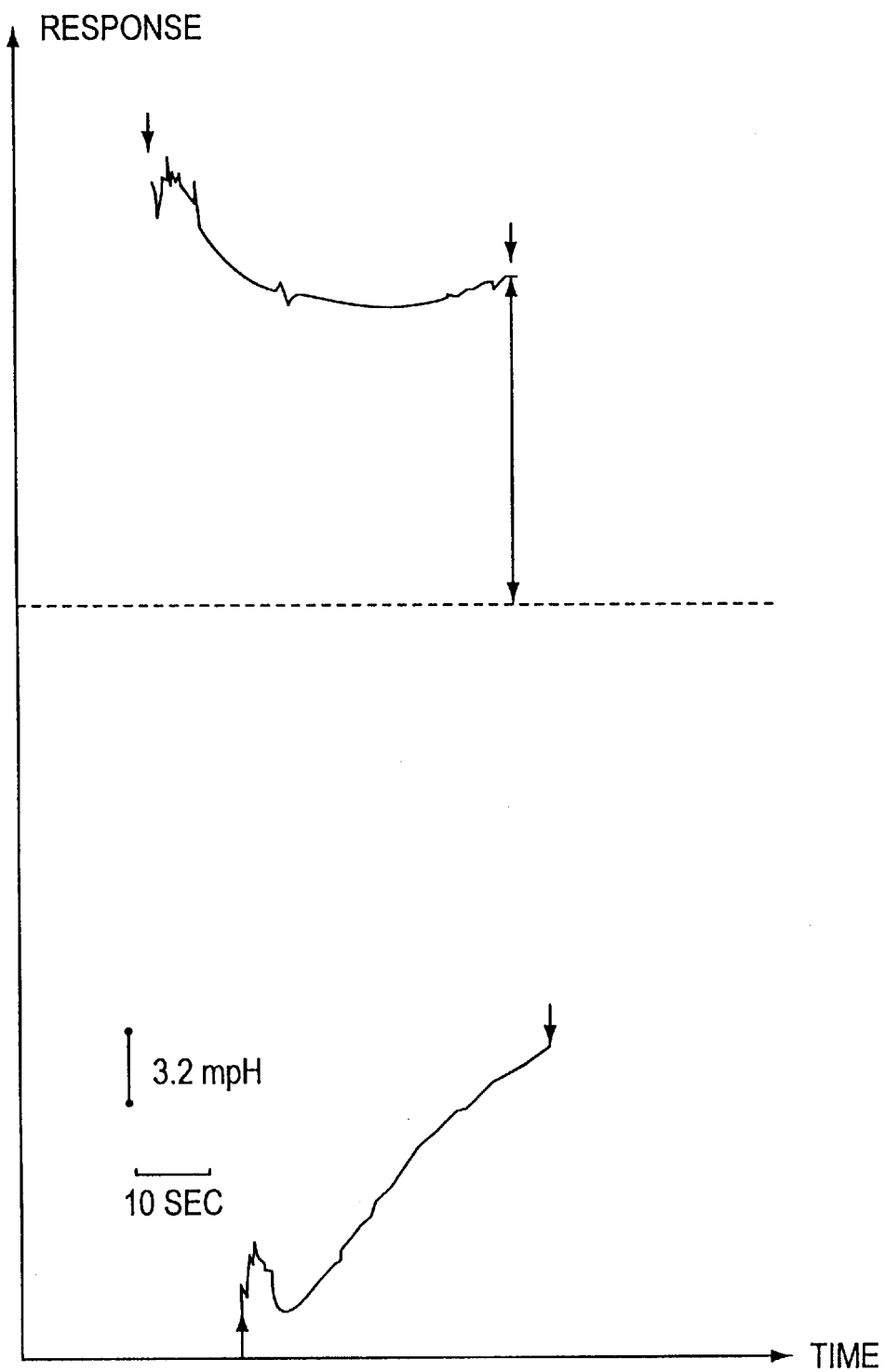
FIG. 1 shows the responses of an uncontaminated pH electrode and of a protein contaminated pH electrode, respectively, on exposure to whole blood, FIG: 2 shows the responses of a protein contaminated pH electrode on exposure to a first liquid having a controlled pH value and comprising no added $Ca^{++}$ ions and to a second liquid having a controlled pH value and comprising added $Ca^{++}$ ions.

It appears from FIG. 1 that there is a clear difference between the responses obtained with a contaminated electrode and an uncontaminated electrode. A pH difference of 35 mpH was found at the time of measurement.

The contaminated pH electrode used for performing the measurements was made in the laboratory by placing one drop of silicone defoaming agent sold by Radiometer A/S under the trade designation S5109 and one drop of lipid containing serum on the pH sensitive membrane of the pH electrode and allowing the electrode membrane to dry overnight. Thereby, a protein or rather a protein/lipid contamination simulating the contamination found on the pH electrode membrane in inadequately cleaned analyzers is obtained.

Figure 2:
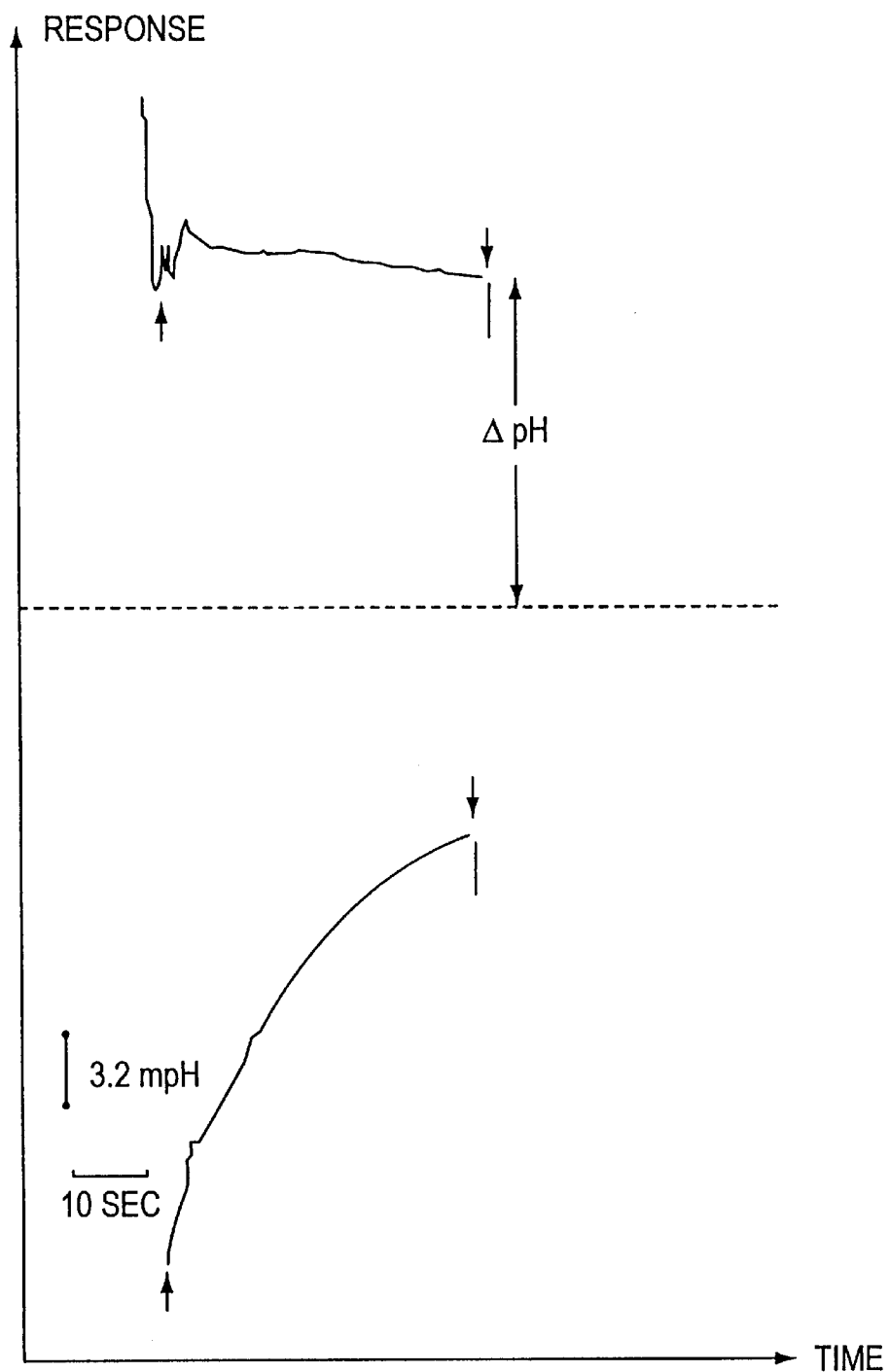

FIG. 2 shows similarly the responses obtained with a contaminated electrode on two synthetic samples each having a controlled pH value. The contaminated electrode was prepared as previously described.

The sample used for the measurements leading to the upper curve was an aqueous solution of the EPPS buffer (90 mmol/l) having an ion strength of I=0.16 obtained by addition of the necessary amount of NaCl. A stable response is obtained very soon after the formation of the liquid junction as indicated by the arrow to the left. The sample used for the measurements leading to the lower curve was an aqueous solution of the EPPS buffer (90 mmol/l further comprising 2 mmol/l $CaCl_2$ and having on ion strength of I=0.16 obtained by addition of the necessary amount of sodium chloride. An electrode response very similar to the electrode response obtained on whole blood is seen. The responses at the time of measurement differs 26 mpH, i. e. the difference is greater than the $\Delta pH_{ass}$ of 15 mpH often specified for aqueous quality control liquids.

Figure 3:
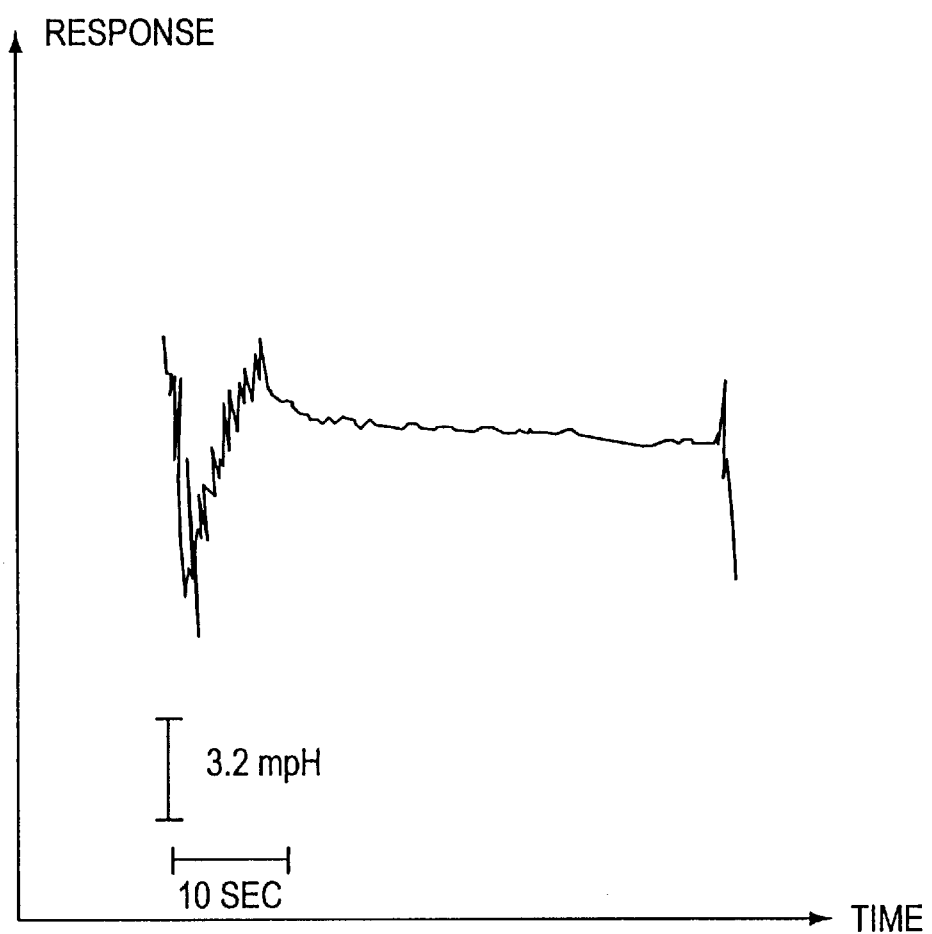
FIG. 3 shows the response of a protein contaminated pH electrode on exposure to a liquid having a controlled pH value and comprising added protein.

FIG. 3 shows the pH electrode response obtained with a contaminated pH electrode in a similar manner as explained in connection with the previous drawings.

The sample was an aqueous solution of the HEPES buffer (93 mmol/l, I=0.16) containing 7 g albumin/100 ml. An electrode response very similar to the electrode response obtained with the EPPS buffer solution without added calcium chloride is seen.

The addition of protein (albumin) does not make the synthetic buffer solution behave like blood when exposed to a contaminated pH electrode. This finding is contrary to the general understanding in the art, cf. for example the previous mentioned Elser article.

Figure 4:
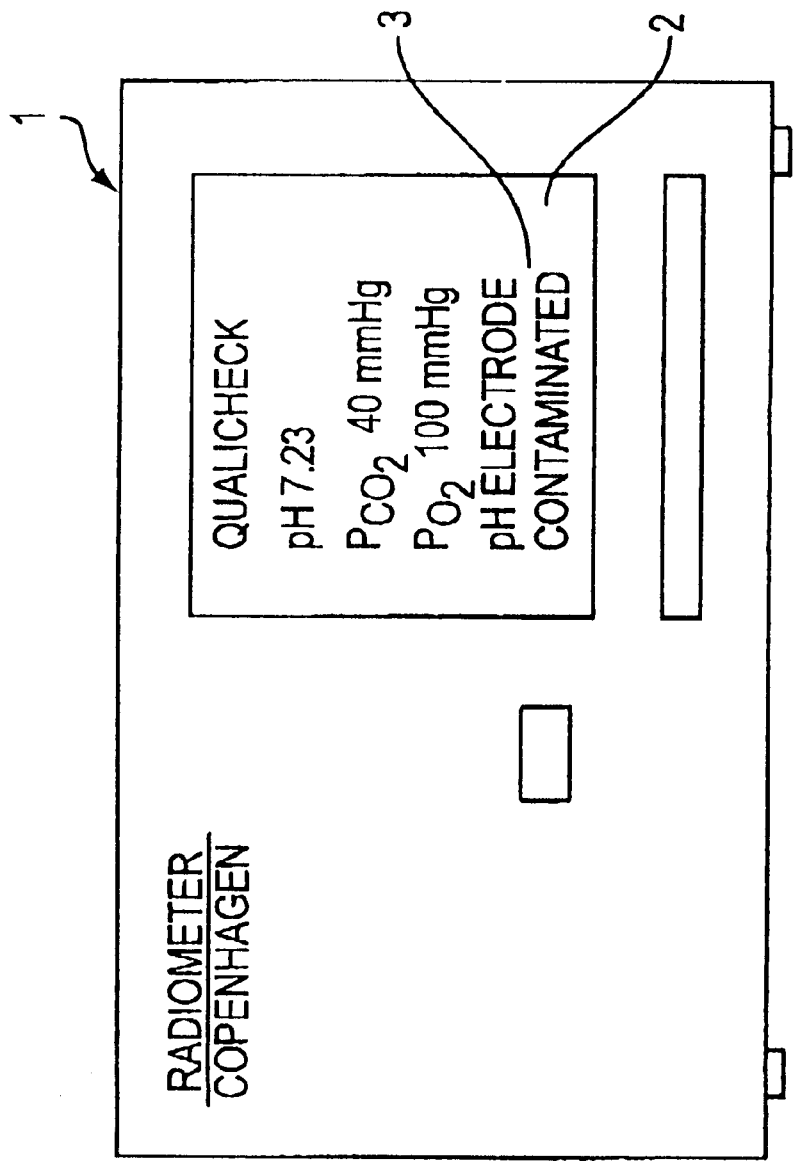
FIG.4 is a schematic representation of an analyzer according to the invention.

FIG. 4 shows a schematic representation of an automated blood gas analyzer according to the invention and generally designated 1. The analyzer is provided with a screen 2 and is adapted to cooperate with a quality control liquid containing an effective amount of $Ca^{++}$.

The analyzer is provided with means for indicating the presence of protein contamination on the pH electrode in the form of the message shown as 3 on screen 2.

Otherwise the analyzer is well known in the art.

The examples given below illustrate the composition and the preparation of a quality control system according to the invention.

The particular chemicals referred to in the examples and in the description of the drawing are the following:

HEPES: N-2-Hydroxyethyl piperazine-N'-2-ethane sulphonic acid from Sigma Chemical Company No. H-3375;

EPPS: N-2-Hydroxyethyl piperazine-N'-3-propane sulphonic acid from Sigma Chemical Company No. E-9502;

Tricine: $(HOCH_2)_3$ $C-^{30}$ $NH_2-CH_2-COO^-$ from Sigma Chemical Company No. E9502;

NaCl krist. zur Analyse from Merck No. 6404; KCl zur Analyse from Merck No. 4936; NaOH Plätchen zur Analyse from Merck No. 6498; $CaCl_2, 2H_2O$ krist. zur Analyse from Merck No. 2382; $NaHCO_3$ zur Analyse from Merck No. 6329; Polyethylene oxide MW ca. 300,000 from BDH Chemicals Ltd.,.England No. 29760; Synperonic NP 35 Surface Active Agents from ICI; Fluorinert® FC43 Electronic Liquid from 3M.

Example 1

Quality Control System according to the Invention

A liquid quality control system according to the invention comprises 4 liquids of the compositions indicated in tables 1–4, respectively, below:

TABLE 1

Quality control composition of pH 7.1;
$Po_2$ 55 mm Hg; $Pco_2$ 60 mm Hg.

A first liquid has the composition set forth in Table 1 below:

| | | |
|---|---|---|
| HEPES | 77.71 mmol/l | 18.518 g/l |
| NaCl | 112.679 mmol/l | 6.5861 g/l |
| KCl | 7.00 mmol/l | 0.522 g/l |
| NaOH | 36.881 mmol/l | 1.475 g/l |
| $CaCl_2, 2H_2O$ | 2.14 mmol/l | 0.3144 g/l |
| Polyethylene oxide, MW 300,000 | | 2.5 g/l |
| Synperonic NP35 | | 10.0 g/l |
| Fluorinert ® FC43 | | 200 g/l |
| $NaHCO_3$ | 20.44 mmol/l | 1.716 g/l |

TABLE 2

Quality control compositon of pH 7.4;
$Po_2$ 100 mm Hg; $Pco_2$ 40 mm Hg.

A second liquid has the composition set forth in Table 2 below:

| | | |
|---|---|---|
| HEPES | 66.540 mmol/l | 15.856 g/l |
| NaCl | 89.492 mmol/l | 5.2308 g/l |
| KCl | 4.00 mmol/l | 0.2942 g/l |
| NaOH | 37.565 mmol/l | 1.4643 g/l |
| $CaCl_2, 2H_2O$ | 1.84 mmol/l | 0.270 g/l |
| Polyethylene oxide, MW 300,000 | | 2.5 g/l |
| Synperonic NP35 | | 10.0 g/l |
| Fluorinert ® FC43 | | 200 g/l |
| $NaHCO_3$ | 25.263 mmol/l | 2.1221 g/l |

TABLE 3

Quality control composition of pH 7.6;
$Po_2$ 160 mm Hg; $Pco_2$ 20 mm Hg.

A further liquid has the composition set forth in Table 3 below:

| | | |
|---|---|---|
| Tricine | 50 mmol/l | 8.9600 g/l |
| NaCl | 94.09 mmol/l | 5.499 g/l |
| KCl | 2.5 mmol/l | 0.1864 g/l |
| NaOH | 18.070 mmol/l | 0.5199 g/l |
| $CaCl_2, 2H_2O$ | 2.57 mmol/l | 0.3780 g/l |
| Polyethylene oxide, MW 300,000 | | 2.5 g/l |
| Synperonic NP35 | | 10.0 g/l |
| Fluorinert ® FC43 | | 50 g/l |
| $NaHCO_3$ | 20.40 mmol/l | 1.713 g/l |

TABLE 4

Quality control composition of pH 7.1;
$Po_2$ 350 mmHg; $Pco_2$ 100 mmHg.

A fourth liquid has the composition set forth in Table 4 below:

| | | |
|---|---|---|
| MOPS | 34.538 mmol/l | 8.230 g/l |
| NaCl | 75.461 mmol/l | 4.4107 g/l |
| KCl | 2.5 mmol/l | 0.1864 g/l |
| NaOH | 13.979 mmol/l | 0.559 g/l |
| $NaHCO_3$ | 30.56 mmol/l | 2.567 g/l |
| Polyethylene oxide, MW 300.000 | | 1.2500 g/l |

The liquids are packaged in glass ampoules under a controlled gas phase consisting of oxygen, carbon dioxide and nitrogen. The particular pH, $Pco_2$ and $Po_2$ measurement values to be expected when using the liquid in connection with particular blood gas measurement apparatuses are established in a manner known per se and provided as an information accompanying the ampoules.

Each of the compositions according to tables 1–4 may optionally comprise further ingredients such as dyes, germicides, surface active agents and the like.

Example 2

Preparation of a Liquid Quality Control Composition

The compositions identified in Tables 1–4 are reported by the following procedure:

A: Preparation of 5 liter aqueous buffer solution Synperonic NP35 and polyethylene oxide each in the amount per liter composition indicated for the respective composition are added to a first portion of water of about 1 l (liter). The mixture is allowed to stand overnight in order to ensure complete dissolution.

NaCl, KCl, NaOH and $CaCl_2$ each in the amount per liter composition indicated for the respective composition are dissolved in a second portion of water of about 2 l (liter).

Water up to 4.75 l (liter) is added.

B: Preparation of emulsion

A Gaulin Laboratory Homogenizer, model 15 M, Gaulin Corporation, Mass. is used. A droplet size less than 1 αm is aimed at. The pressure used is 500 $kg/cm^2$.

The required amount of Fluorinert® FC43 (1 kg) was circulated in the homogenizer and buffer solution prepared as described in Part A was added slowly. After completion of the addition of the buffer solution the homogenizer was switched from the recirculation mode to a run-through mode and the mixture was passed through the homogenizer 4 times.

Finally, the required amount of sodium bicarbonate dissolved in 0.25 l (liter) water was added and the mixture was thoroughly shaken.

I claim:

1. A method for revealing the presence of protein contamination on the measuring surface of a pH measuring electrode, comprising the steps of:

contacting the pH measuring electrode with a synthetic quality control liquid having a controlled specified pH value and comprising an amount of cations selected from the group consisting of $Ca^{+2}$, $Cu^{+2}$, $Fe^{+2}$ and $Co^{+2}$ greater than 0.1 mmol/l., said amount being sufficient to shift the pH response of a protein contaminated pH electrode to a value different from the specified pH value of the quality control liquid;

comparing the pH value measured for the quality control liquid with the specified pH value; and using the outcome of the comparison to indicate whether or not protein contamination is present, taking a lower measured pH value than the specified pH value as an indication of the presence of protein contamination on the measuring surface of the pH measuring electrode.

2. The method of claim 1, additionally comprising:

contacting the measuring surface of the pH measuring electrode with a second quality control liquid having a controlled specified pH value and comprising an amount of cations selected from the group consisting of $Ca^{+2}$, $Cu^{+2}$, $Fe^{+2}$ and $Co^{+2}$ less than 0.5 mmol/l., said amount being lower than the minimum amount effective to shift the pH response of a contaminated pH electrode to a value different from the pH value specified for said second quality control liquid; and comparing the pH value measured for the second quality control liquid with the pH value specified therefor;

the determination of a lower measured pH value than the specified pH value for the first quality control liquid and a measured pH value corresponding to the specified pH value for the second quality control liquid indicating the presence of protein contamination on the measuring surface of the pH measuring electrode.

3. The method of claim 2, in which the second quality control liquid essentially excludes any added $Ca^{+2}$ ions.

* * * * *

UNITED STATES PATENT AND TRADEMARK OFFICE
CERTIFICATE OF CORRECTION

PATENT NO : 5,910,445

DATED : June 8, 1999

INVENTOR : Eiler LARSEN

It is certified that error appears in the above-identified patent and that said Letters Patent is hereby corrected as shown below:

On the title page, under "[73] Assignee," please delete "Rolic AG, Zug, Switzerland."

Signed and Sealed this

Fifth Day of December, 2000

Attest:

Q. TODD DICKINSON

*Attesting Officer*  *Director of Patents and Trademarks*